(12) United States Patent
Felzmann et al.

(10) Patent No.: US 9,051,336 B2
(45) Date of Patent: Jun. 9, 2015

(54) REGIOSELECTIVE ACYLATION OF RAPAMYCIN AT THE C-42 POSITION

(75) Inventors: Wolfgang Felzmann, Kundl (AT); Niklas Schone, Kundl (AT)

(73) Assignee: SANDOZ, Basel (CH)

( * ) Notice: Subject to any disclaimer, the term of this patent is extended or adjusted under 35 U.S.C. 154(b) by 0 days.

(21) Appl. No.: 14/005,678

(22) PCT Filed: Mar. 30, 2012

(86) PCT No.: PCT/EP2012/055757
§ 371 (c)(1),
(2), (4) Date: Dec. 2, 2013

(87) PCT Pub. No.: WO2012/131019
PCT Pub. Date: Oct. 4, 2012

(65) Prior Publication Data
US 2014/0081016 A1    Mar. 20, 2014

(30) Foreign Application Priority Data
Apr. 1, 2011   (EP) ..................................... 11160858

(51) Int. Cl.
*C07D 498/18* (2006.01)
*C07D 498/14* (2006.01)

(52) U.S. Cl.
CPC ............ *C07D 498/14* (2013.01); *C07D 498/18* (2013.01)

(58) Field of Classification Search
CPC .................................................... C07D 498/18
USPC ......................................... 540/456
See application file for complete search history.

(56) References Cited

U.S. PATENT DOCUMENTS

| | | | |
|---|---|---|---|
| 4,316,885 A | 2/1982 | Rakhit | |
| 5,120,727 A | 6/1992 | Kao | |
| 5,362,718 A | 11/1994 | Skotnicki | |
| 6,277,983 B1 * | 8/2001 | Shaw et al. | 540/456 |
| 2007/0129541 A1 | 6/2007 | Zhang | |
| 2010/0249415 A1 | 9/2010 | Lee | |

FOREIGN PATENT DOCUMENTS

| | | |
|---|---|---|
| EP | 1266899 A2 | 12/2002 |
| WO | 95/28406 A1 | 10/1995 |
| WO | 2005/100366 A1 | 10/2005 |

OTHER PUBLICATIONS

International Search Report issued Apr. 27, 2012 in PCT/EP2012/055757.
Sorbera, et. al., "CCI-779: Oncolytic mTOR inhibitor," Drugs of the Future, Prous Science, ES, vol. 27, No. 1, Jan. 1, 2002, pp. 7-13.

* cited by examiner

*Primary Examiner* — Bruck Kifle
(74) *Attorney, Agent, or Firm* — Jeffrey S. Melcher; Manelli Selter PLLC

(57) ABSTRACT

The invention refers to the selective acylation of Rapamycin at the 42-position (I) with an acylating agent of the formula (II) wherein $R^4$ and $R^5$ are the same or different, individually the rest of an acetal, especially tetrahydropyran, or of a carbonate or the rest of a silyl ether or taken together are the rest of a boronate, an acetal or ketal.

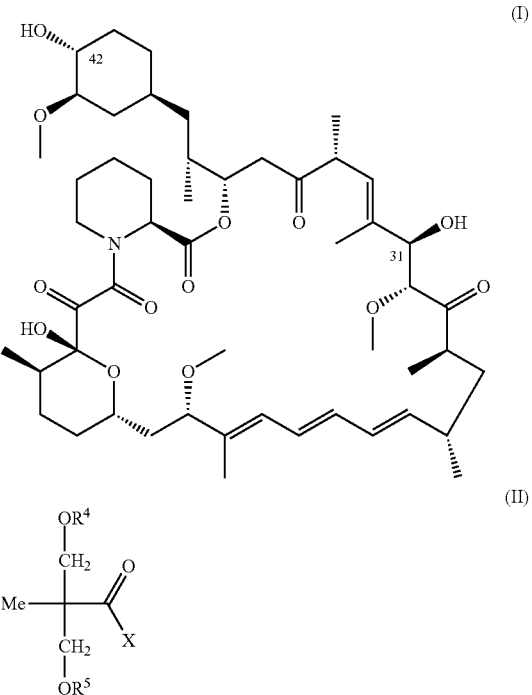

18 Claims, No Drawings

REGIOSELECTIVE ACYLATION OF RAPAMYCIN AT THE C-42 POSITION

The present invention refers to the acylation of Rapamycin, especially to a regioselective acylation of Rapamycin.

Rapamycin (1) is an immunosuppressant drug used to prevent rejection in organ transplantation. It is a macrolide of the following formula:

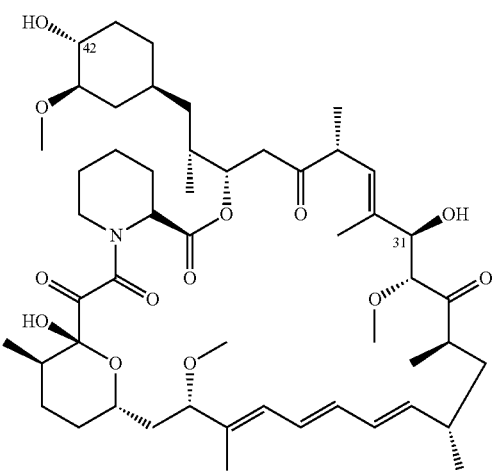

Rapamycin (1) is an intermediate for the production of temsirolimus which is a drug for the treatment of renal cell carcinoma. Temsirolimus has the following formula:

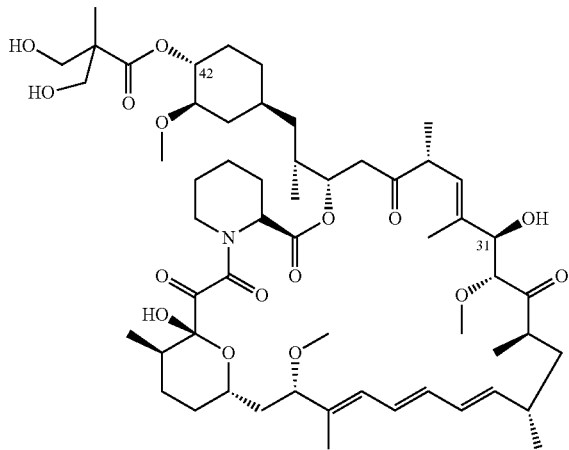

For the preparation of Temsirolimus (2), Rapamycin (1) has to be acylated in the 42-position.

According to WO 95/28406 A1 Rapamycin may be acylated by an acylating agent, e.g. the mixed anhydride of 2,2,5-trimethyl[1,3]dioxane-5-carboxylic acid with 2,4,6-trichlorobenzoic acid in the presence of 4-dimethylaminopyridine (DMAP), but only mediocre yields are obtained. According to WO 2005/100366 A1 a method for the regiospecific preparation of a Rapamycin 42-ester comprises reacting Rapamycin with an activated ester in the presence of an effective amount of a microbial lipase. According to US2010/0249415 Rapamycin can be acylated using 2,2,5-trimethyl[1,3]dioxane-5-carboxylic acid anhydride in the presence of DMAP; as stated therein, "it becomes a tough challenge to effectively discriminate these two functional centers in order to achieve a selective synthesis of 42-monoacylated product"—hence, this process is conducted at low conversion rates (<40%) to achieve good selectivity but low amounts of degradation by-products.

According to U.S. Pat. No. 4,316,885 acyl derivatives of Rapamycin are prepared by adding acetic anhydride to a solution of Rapamycin in pyridine. However, the yield for the desired 42-acetyl-derivative is lower than the yield for the bis-acyl derivative, which is the undesired predominant product.

According to U.S. Pat. No. 5,120,727 dicarboxylic acid chlorides are added to solutions of Rapamycin in toluene. Again, the yields and selectivity for the desired 42-acyl derivative are low.

The known processes are not satisfactory concerning yield, costs and equivalents of reagent.

Therefore, an object of the present invention is to provide a method for the acylation of macrolactone polyketides, especially Rapamycin, with improvements concerning yield, cost and/or equivalents of reagents. A further object of this present invention is to provide a method of acylation of macrolactone polyketides with improved regioselectivity.

Regioselectivity herein is understood as the selectivity of a chemical transformation to take place at only one specific functional group in a molecule bearing more than one such functional groups.

The present invention refers to a method for the acylation of Rapamycin with an acylating agent of the formula

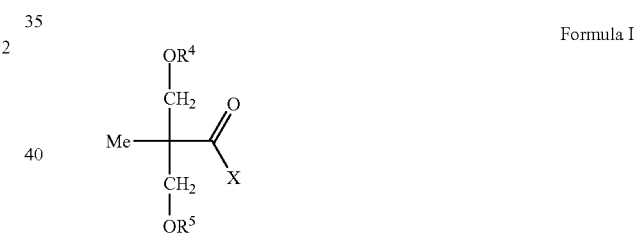

Formula I wherein $R^4$ and $R^5$ are the same or different, individually the rest of an acetal, especially tetrahydropyran, or of a carbonate or the rest of a silyl ether or taken together are the rest of a boronate, an acetal or ketal, preferably a ketal of formula II

Formula II wherein $R^6$ are each, independently H, methyl, ethyl, propyl, phenyl or can be taken together to form a cyclobutane, cyclopentane, cyclohexane, cycloheptane or cyclooctane ring, and X is an halogen, more specifically F, Cl or Br,
in the presence of a base which is pyridine, optionally in the presence of an additional solvent S.

According to the present invention, conversion and selectivity concerning the acylation of Rapamycin can be improved. Especially, the acylation of the 42-position of Rapamycin is improved concerning high conversion rate in combination with high selectivity.

For the evaluation of different acylation conditions the following criteria are defined:

Conversion refers to the ratio of area % 3/(area % 3+area % 1)

Selectivity refers to the ratio of area % 3/(area % 3+area % 4)

Bold numbers refer to the compounds as defined hereinafter and
area % refers to the area of one specific peak relative to the sum of all peaks in a chromatogram.

Yield refers to the amount of pure compound present after purification and isolation, indicated as the fraction moles (product):moles (substrate)

The term substrate refers to the chemical species under observation in the reaction, herein normally Rapamycin or a derivative thereof.

The term equivalent refers to the molar ratio of a given compound to the substrate.

The acylating agents useful for this invention are depicted in formula I. In one embodiment the substituents of formula I have the following meaning:
$R^4$, $R^5$: are a ketal of formula II

Formula II wherein
$R^6$: are each, independently H, methyl, ethyl, propyl, phenyl or can be taken together to form a cyclopentane or cycloheptane ring, and
X: is halogen, preferably Br, F or, most preferred, Cl.

In a preferred embodiment, the substituents have the following meaning:
$R^4$, $R^5$: are a ketal of formula II

Formula II wherein
$R^6$: are methyl, ethyl or taken together to form a cyclopentane or cycloheptane ring, and
X: is halogen, preferably Br, F or, most preferred, Cl.

In one particular preferred embodiment the acylating agent is 2,2,5-trimethyl[1,3]dioxane-5-carboxylic acid chloride (TMDC-Cl).

The used base is pyridine.

The equivalents of base used in the process can be 1-10 equivalents, more preferably 3-6 equivalents.

The acylation is preferably conducted in the presence of solvents, in particular organic solvents defined as non-protic, polar solvents. Useful solvents are $CH_2Cl_2$, chloroform, tetrahydrofuran, 2-methyltetrahydrofuran, dioxane, methyl acetate, ethyl acetate, methyl propionate, ethyl propionate, n-propyl acetate, isopropyl acetate, or mixtures thereof. Pyridine may be used both as base and as solvent.

The acylation may be conducted in a temperature range of −5 to 20° C., in particular at 2 to 8° C. The substrate concentration may be from 0.05 to 0.5 moles per liter of solvent, in particular of from 0.1 to 0.3 moles per liter of solvent. In a preferred embodiment 1.0 to 10 equivalents, in particular 2.0 to 3.0 equivalents of the acylating agent is used.

In one preferred embodiment the present invention refers to the acylation of Rapamycin in the 42-position with the 2,2,5-trimethyl-1,3-dioxane-5-carboxylic acid chloride in the presence of pyridine as base, most preferred at a temperature of from −5 to 20° C., especially from 2 to 8° C.

Purification of Compound 3

The optional purification of the acylated compound 3 can be achieved using standard laboratory techniques, like column chromatography and crystallization. As a subject of this invention, crystallization of the product from a mixture of heptane and ethyl acetate, a product with strength>90% can be obtained. Furthermore, the content of the bis-acylated by-product<4.0% and the content of the starting material is <0.05%

The following is to illustrate the preparation of representative compounds of this invention.

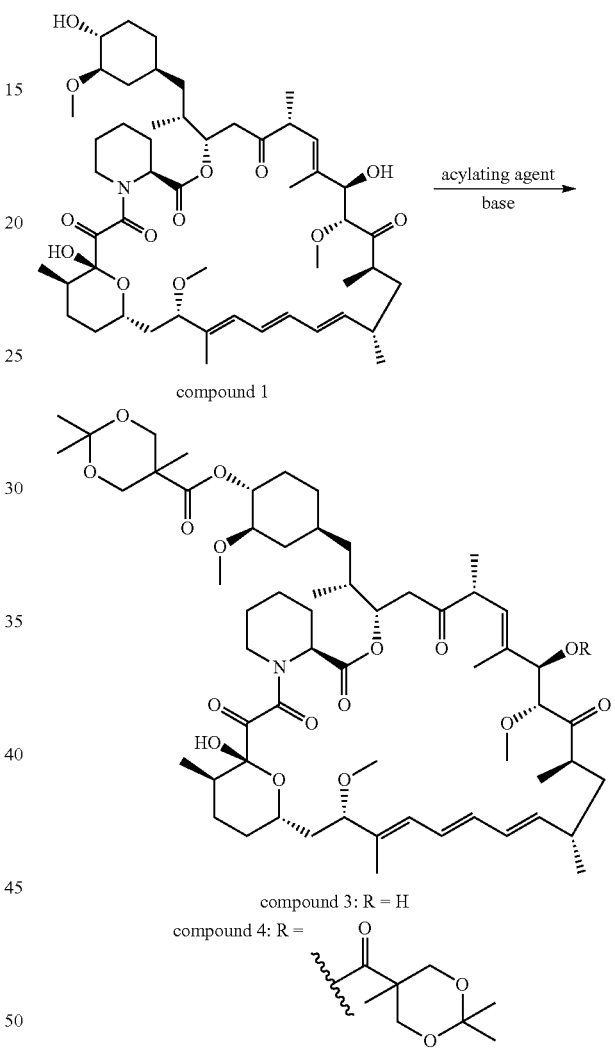

compound 1 compound 3: R = H
compound 4: R =

Above shown illustration is a preferred embodiment, wherein the strength of product 3 is >95%. In a particular preferred embodiment, the content of compound 4 is <2.0% and the content of compound 1 is <0.05%.

A high amount of purity/low impurity level of the compound obtained in this acylation step is of high importance for the purity of consecutive reaction products obtained by removal of the protecting groups. Especially the presence of the bis-acylated product leads to impurities in the product which are hard to remove by chromatography and/or crystallization.

In a further embodiment, the reaction product of acid hydrolysis (deprotection) of compound 3 is temsirolimus (2).

The by-product from the hydrolysis of compound 4 is a compound characterized as 31-(2,2,5-trimethyl-1,3-dioxane-5-carboxylate)-temsirolimus Purification of Compound 2

The optional purification of compound 2 can be achieved using standard laboratory techniques, like column chromatography and crystallization. As a subject of this invention, crystallization of the product from a mixture of heptane and ethyl acetate, a product with strength>90% can be obtained. In a preferred embodiment, the strength is >95%. In a particular preferred embodiment, the content of 31-(2,2,5-trimethyl-1,3-dioxane-5-carboxylate)-temsirolimus is <0.15%.

To obtain even higher purity, purification by pHPLC can be used to achieve purities>98%. Said method also allows to remove a concomitant by-product from fermentation, 36-Desmethyl-36-ethyl-temsirolimus. In a preferred embodiment of this invention, the content of 36-Desmethyl-36-ethyl-temsirolimus is <0.15 area % in the final product.

With these criteria, the following experiment was used to test the different conditions:

EXAMPLE 1

Rapamycin 42-ester with
2,2,5-trimethyl[1,3]dioxane-5-carboxylic acid (3)

1.00 g Rapamycin were solved in 2-10 ml $CH_2Cl_2$ to achieve the concentration indicated in Table 1 and mixed with the reagent and base in the quantities indicated in the following Table 1 and stirred and maintained at the temperature given in Table 1. The mixture was stirred for 3 days or until reaction control showed full conversion. Precipitates of amine hydrochlorides were removed by filtration, and the filter washed with 20 mL $CH_2Cl_2$. The filtrate was washed with 20 ml water, dried over $MgSO_4$, filtered and concentrated in vacuo to obtain the final product.

The following acylating reagents were used wherein TMDC means 2,2,5-trimethyl[1,3]dioxane-5-carboxylic acid:

| Abbreviation | Formula |
|---|---|
| TMDC AE | TMDC mixed anhydride with trichlorobenzoic acid |
| TMDC Cl | TMDC-chloride |
| TMDCA | TMDC-Anhydride |

The following bases were used:

| Full name | Abbreviation |
|---|---|
| 4-Dimethylaminopyridine | DMAP |
| Triethylamine/Dimethylaminopyridine | Et3N/DMAP |
| 4-(N-pyrrolidinyl)-pyridine | PYPY |
| Pyridine | —/— |

Reaction parameters and results have been entered into the following Table 1:

Advantages

Both the combination of the acylating agent and the base, were crucial for the success of this reaction. For example, the significance of the combination of TMDC-Cl with pyridine can be seen by comparison with the data obtained for other acylating agents (Table 1). Especially the use of 4,4-dimethylaminopyridine (DMAP), as used in the prior art, as well as other amine bases and the combination thereof led to much lower selectivities. A further impact has the temperature Table 1 shows that the best results concerning conversion and selectivity have been obtained according to the present invention.

EXAMPLE 2

Rapamycin 42-ester with
2,2,5-trimethyl[1,3]dioxane-5-carboxylic acid (3)

A 500 mL 3-neckflask was charged with rapamycin (25 g, 25.98 mmol) and 70 mL of $CH_2Cl_2$ were added. The solution was then cooled to 5° C. In a separate vessel, TMDC-Cl (12.51 g, 64.95 mmol) was diluted with 28 mL of $CH_2Cl_2$ and then cooled to 5° C. Pyridine (9.73 g, 122.1 mmol) was added and the resulting mixture was added to the rapamycin solution. The resulting mixture was then stirred at 5° C. for 24 h, when reaction control by HPLC showed >97% conversion.

The reaction mixture was quenched by addition of $(NH_4)_2SO_4$-solution. Then 200 mL EtOAc were added and the biphasic mixture was concentrated in vacuo. 100 mL of EtOAc were added, and the reaction mixture was adjusted to pH 2 by addition of 2M $H_2SO_4$. After stirring for 5 min, the aqueous layer was separated and discarded. The organic layer was then washed with 50 mL of $NaHCO_3$-solution and 50 mL of brine. The organic layer was dried over $Na_2SO_4$, filtered and concentrated in vacuo to give a white foam.

Purification was achieved by column chromatography over 660 g $SiO_2$ using heptane/ethyl acetate/1:1. The product was concentrated to ⅓ of the initial volume, where the solution turned turbid. Seeding crystals are added, followed by further concentration. The solid was then filtered off and dried in vacuo to yield 21 g (75%) of compound 3 with a strength>95%, impurified by less than 2.0% of compound 4.

EXAMPLE 3

Temsirolimus (2)

18.3 g of compound 3 were dissolved in 160 mL THF. The resoluting solution was cooled to 5° C. Then 32 mL 2M $H_2SO_4$ were added and the mixture was stirred for 24 h. Then the reaction was neutralized by addition of saturated $NaHCO_3$-solution and extracted with a total of 200 mL ethyl acetate. The organic layer was then washed with half-satu-

TABLE 1

| No. | Comparison/ invention | c(RAPA) [mol/L] | reagent | equiv. | base | equiv. Base | temp. (° C.) | Conversion (%) | Selectivity (%) |
|---|---|---|---|---|---|---|---|---|---|
| 1 | Comparison | 0.21M | TMCD-AE | 2.2 | Et3N/DMAP | 4.0/4.0 | −5° C. | 0.91 | 0.81 |
| 2 | Comparison | 0.40M | TMCD-AE | 2.2 | pyridine | 4.0 | −5° C. | 0.80 | 0.93 |
| 3 | Comparison | 0.10M | TMDC-Cl | 2.2 | Et3N/DMAP | 4.0/2.0 | 5° C. | 0.91 | 0.71 |
| 4 | invention | 0.25M | TMDC-Cl | 2.2 | pyridine | 4.0 | 5° C. | 0.96 | 0.97 |
| 5 | Comparison | 0.13M | TMDCA | 2.1 | Et3N/DMAP | 4.0/2.0 | 5° C. | 0.88 | 0.73 |
| 6 *) | Comparison | 0.13M | TMDCA | 2.1 | pyridine | 4.0 | 5° C. | 0.00 | — |
| 7 | Comparison | 0.25M | TMDCA | 2.1 | PYPY | 4.0 | 5° C. | 0.67 | 0.87 |
| 8 | Comparison | 0.25M | TMDC-AE | 2.0 | DMAP | 1.0 | 20° C. | 0.66 | 0.83 |

*) no reaction observed rated NaCl-solution, dried with $Na_2SO_4$, filtered and concentrated in vacuo to give a white foam. Purification was achieved by column chromatography over 600 g $SiO_2$ using heptane/ethyl acetate/1:3. The product was concentrated to ⅙ of the initial volume, and heptane was added to the reaction vessel dropwise until the solution turned turbid. Seeding crystals were added, followed by further addition of heptane until half of the initial volume is reached. The solid was then filtered off and dried in vacuo to yield 12.85 g (73%) of 2. If desired, further purification of 2 can be achieved by dissolution in heptane:ethyl acetate 65:35 followed by subjection to pHPLC over normal phase silica gel YMC SL06S11 using a mixture of heptane:ethyl acetate 65:35 as mobile phase. Fractioning of the eluate by UV-detection, followed by concentration, seeding and addition of heptane then delivers 2 as a white solid, which can be isolated by filtration, yielding 10.54 g (82%)

The invention also refers to the following embodiments:

(1) A process for the acylation of Rapamycin with an acylating agent of the formula

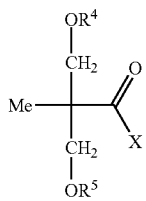

Formula I wherein $R^4$ and $R^5$ are the same or different, individually the rest of an acetal, especially tetrahydropyran, or of a carbonate or the rest of a silyl ether or taken together are the rest of a boronate, an acetal or ketal, preferably a ketal of formula II

Formula II wherein $R^6$ are each, independently H, methyl, ethyl, propyl, phenyl or can be taken together to form a cyclobutane, cyclopentane, cyclohexane, cycloheptane or cyclooctane ring, and X is an halogen, more specifically F, Cl or Br, in the presence of a base which is pyridine, optionally in the presence of an additional solvent S.

(2) The process of item 1, wherein the solvent S is selected from a group consisting of $CH_2Cl_2$, chloroform, tetrahydrofuran, 2-methyltetrahydrofuran, dioxane, methyl acetate, ethyl acetate, methyl propionate, ethyl propionate, n-propyl acetate, isopropyl acetate, or mixtures thereof.

(3) The process of item 1 or 2, wherein in formula I the substituents have the following meanings:
$R^4$, $R^5$: are a ketal of formula II

Formula II $R^6$: are each, independently H, methyl, ethyl, propyl, phenyl or can be taken together to form a cyclopentane or cycloheptane ring X: is halogen, preferably Br, Cl, F or, most preferred, Cl.

(4) The process of any of items 1 to 3, wherein the substituents of formula I have the following meanings:
$R^1$, $R^2$, $R^3$: H
$R^4$, $R^5$: together the group of formula II

Formula II wherein $R^6$ is methyl and X is Cl.

(7) The process of at least one of the preceding items, wherein the acylation is performed at a temperature of from −5 to 20° C., in particular at +5° C.±3° C.

(8) The process of at least one of the preceding items, wherein from 1.0 to 10, in particular from 2.0 to 3.0 mol of the acylating agent is used per mol of the compound to be acylated.

(9) The process of at least one of the preceding items, wherein Rapamycin is acylated in 42-position with 2,2,5-trimethyl-1,3-dioxane-5-carboxylic acid chloride in the presence of pyridine.

(10) The process of at least one of the preceding items, which produces crystalline 42-TMDC-RAPA with strength>95%.

(11) The process of item (10), wherein the content of 31,42-TMDC-RAPA is <2.0% and the content of Rapamycin is <0.05%.

(12) Process for synthesizing temsirolimus using 42-TMDC-RAPA obtained via a process defined in at least one of the preceding items.

(13) Temsirolimus, obtained or obtainable according to the process of at least one of items 10 to 12.

(14) Temsirolimus, containing less than 0.15 area % of 31-(2,2,5-trimethyl-1,3-dioxane-5-carboxylate)-temsirolimus.

(15) Temsirolimus, containing less than 0.15 area % of 36-Desmethyl-36-ethyl-temsirolimus.

The invention claimed is:

1. A process for the acylation of Rapamycin with an acylating agent, the process comprising acylating Rapamycin with an acylating agent of the formula

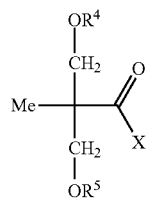

Formula I wherein $R^4$ and $R^5$ are chosen to provide an acylating agent selected from the group consisting of:

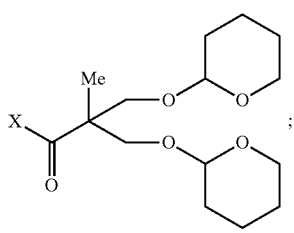

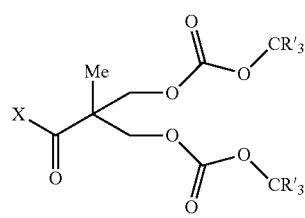

wherein R' are each, independently selected from the group consisting of H, methyl, ethyl, and propyl;

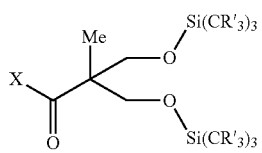

wherein R' are each, independently selected from the group consisting of H, methyl, ethyl, and propyl;

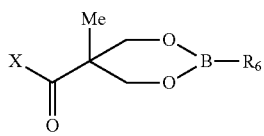

wherein $R^6$ is selected from the group consisting of methyl, ethyl, propyl, and phenyl;

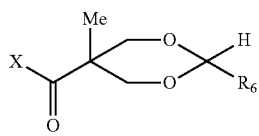

wherein $R^6$ is selected from the group consisting of methyl, ethyl, propyl, and phenyl; and

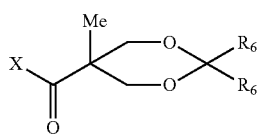

wherein $R^6$ are each, independently methyl, ethyl, propyl, phenyl or can be taken together to form a cyclobutane, cyclopentane, cyclohexane, cycloheptane or cyclooctane ring; and X is an halogen, in the presence of a base comprising pyridine, and optionally in the presence of an additional solvent S.

2. The process of claim 1, wherein the solvent S is selected from a group consisting of $CH_2Cl_2$, chloroform, tetrahydrofuran, 2-methyltetrahydrofuran, dioxane, methyl acetate, ethyl acetate, methyl propionate, ethyl propionate, n-propyl acetate, isopropyl acetate, or mixtures thereof.

3. The process of claim 1, wherein the acylating agent is as follows:

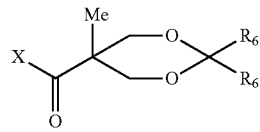

wherein $R^6$ are each independently methyl, ethyl, propyl, phenyl or can be taken together to form a cyclobutane, cyclopentane, cyclohexane, cycloheptane, or cyclooctane ring.

4. The process of claim 1, wherein the acylating agent is as follows:

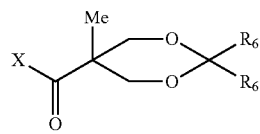

wherein $R^6$ is methyl and X is Cl.

5. The process of claim 1, further comprising performing the acylation at a temperature of from −5 to 20° C.

6. The process of claim 1, from 1.0 to 10 mol of the acylating agent per mol of the compound to be acylated.

7. The process of claim 1, further comprising acylating Rapamycin in 42-position with 2,2,5-trimethyl-1,3-dioxane-5-carboxylic acid chloride in the presence of pyridine.

8. The process of claim 1, further comprising producing crystalline Rapamycin 42-(2,2,5-trimethyl-1,3-dioxane-5-carboxylate) with a purity of >95%.

9. The process of claim 8, wherein the content of Rapamycin 31,42-bis(2,2,5-trimethyl-1,3-dioxane-5-carboxylate) is <2.0% and the content of Rapamycin is <0.05%.

10. Process for synthesizing temsirolimus comprising preparing Rapamycin 42-(2,2,5-trimethyl-1,3-dioxane-5-carboxylate), wherein said Rapamycin 42-(2,2,5-trimethyl-1,3-dioxane-5-carboxylate) is prepared by a process comprising acylating Rapamycin with an acylating agent of the formula Formula I

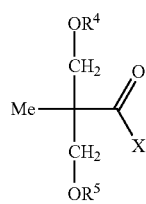

wherein $R^4$ and $R^5$ are chosen to provide an acylating agent selected from the group consisting of:

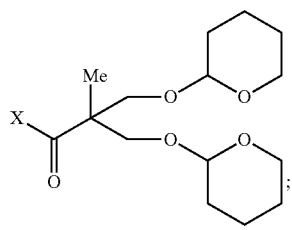

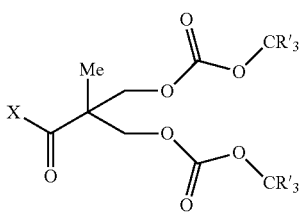

wherein R' are each, independently selected from the group consisting of H, methyl, ethyl, and propyl;

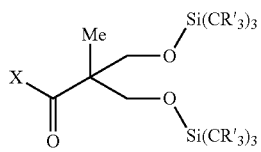

wherein R' are each, independently selected from the group consisting of H, methyl, ethyl, and propyl;

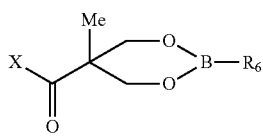

wherein $R^6$ is selected from the group consisting of methyl, ethyl, propyl, and phenyl;

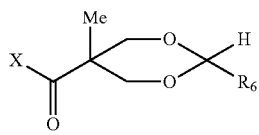

wherein $R^6$ is selected from the group consisting of methyl, ethyl, propyl, and phenyl; and

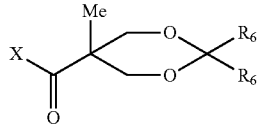

wherein $R^6$ are each, independently methyl, ethyl, propyl, phenyl or can be taken together to form a cyclobutane, cyclopentane, cyclohexane, cycloheptane or cyclooctane ring; and X is an halogen, in the presence of a base comprising pyridine, and optionally in the presence of an additional solvent S.

11. The process of claim 10, further comprising performing acid hydrolysis of said Rapamycin 42-(2,2,5-trimethyl-1,3-dioxane-5-carboxylate) to obtain temsirolimus.

12. The process of claim 1, wherein $R^4$ and $R^5$ are the same or different, $R^4$ and $R^5$ individually as —$CH_2OR^4$ and —$CH_2OR^5$ each represents a tetrahydropyran acetal.

13. The process of claim 1, wherein the acylating agent is as follows:

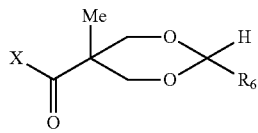

wherein $R^6$ is selected from the group consisting of methyl, ethyl, propyl, and phenyl.

14. The process of claim 1, wherein X is F, Cl or Br.

15. The process of claim 3, wherein X is Br, Cl, F.

16. The process of claim 3, wherein X is Cl.

17. The process of claim 1, further comprising performing the acylation at a temperature of +5° C.±3° C.

18. The process of claim 1, further comprising using from 2.0 to 3.0 mol of the acylating agent per mol of the compound to be acylated.

* * * * *